US009759707B2

(12) United States Patent
Pearl, Jr. et al.

(10) Patent No.: US 9,759,707 B2
(45) Date of Patent: Sep. 12, 2017

(54) SYSTEMS AND METHODS FOR ANALYZING THE CHARACTERISTICS AND COMPOSITIONS OF A DRY CEMENT

(71) Applicant: Halliburton Energy Services, Inc., Houston, TX (US)

(72) Inventors: William Ceceil Pearl, Jr., The Woodlands, TX (US); Megan Renee Pearl, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 120 days.

(21) Appl. No.: 14/890,650

(22) PCT Filed: Sep. 26, 2013

(86) PCT No.: PCT/US2013/061913
§ 371 (c)(1),
(2) Date: Nov. 12, 2015

(87) PCT Pub. No.: WO2015/047275
PCT Pub. Date: Apr. 2, 2015

(65) Prior Publication Data
US 2016/0091478 A1    Mar. 31, 2016

(51) Int. Cl.
*G01N 33/38* (2006.01)
*C09K 8/42* (2006.01)
(Continued)

(52) U.S. Cl.
CPC ....... *G01N 33/383* (2013.01); *C04B 40/0032* (2013.01); *C09K 8/42* (2013.01);
(Continued)

(58) Field of Classification Search
CPC .... G01N 33/383; G01N 21/255; G01N 21/17; G01N 21/84; G01N 2201/12; C09K 8/42; C04B 40/0032
(Continued)

(56) References Cited

U.S. PATENT DOCUMENTS 7,468,520 B1    12/2008    Varmette et al.
7,697,141 B2    4/2010    Jones et al.
(Continued)

FOREIGN PATENT DOCUMENTS

GB    1169387 A    11/1969
WO    2015047275 A1    4/2015

OTHER PUBLICATIONS

Gineys et al., "Managing Trace Elements in Portland Cement—Part I: Interactions Between Cement Paste and Heavy Metals Added During Mixing as Soluble Salts," Cement & Concrete Composites 32 (2010) 563-570.
(Continued)

*Primary Examiner* — Seung C Sohn
(74) *Attorney, Agent, or Firm* — McDermott Will & Emery LLP

(57) ABSTRACT

Optical analysis systems and methods that utilize integrated computational elements ("ICE") may be useful for characterizing dry cements and determining cement slurry additives suitable for use therewith. For example, a method may include optically interacting a dry cement with an ICE configured to detect a characteristic of the dry cement; generating a plurality of output signals corresponding to the characteristic of the dry cement detected by the ICE; receiving and processing the plurality of output signals with a signal processor to yield a value for the characteristic of the dry cement; and determining at least one of a composition and a concentration of a cement slurry additive for use in
(Continued)

combination with the dry cement based on the value of the characteristic of the dry cement.

20 Claims, 2 Drawing Sheets

(51) Int. Cl.
    *G01N 21/25*     (2006.01)
    *C04B 40/00*     (2006.01)
    *G01N 21/17*     (2006.01)
    *G01N 21/84*     (2006.01)

(52) U.S. Cl.
    CPC ........... *G01N 21/17* (2013.01); *G01N 21/255* (2013.01); *G01N 21/84* (2013.01); *G01N 2201/12* (2013.01)

(58) Field of Classification Search
    USPC .......................................... 250/206; 356/326
    See application file for complete search history.

(56) References Cited

U.S. PATENT DOCUMENTS

| | | |
|---|---|---|
| 8,049,881 B2 | 11/2011 | Myrick et al. |
| 9,228,940 B2 * | 1/2016 | Pelletier .................. G01N 21/47 |
| 2010/0302539 A1 * | 12/2010 | Myrick ..................... G01J 3/02 |
| | | 356/326 |
| 2013/0035262 A1 | 2/2013 | Freese et al. |

OTHER PUBLICATIONS

Gineys et al., "Managing Trace Elements in Portland Cement—Part II: Comparison of Two Methods to Incorporate Zn in a Cement," Cement & Concrete Composites 33 (3011) 629-636.

International Search Report and Written Opinion for PCT/US2013/061913 dated Jun. 25, 2014.

* cited by examiner

SYSTEMS AND METHODS FOR ANALYZING THE CHARACTERISTICS AND COMPOSITIONS OF A DRY CEMENT

BACKGROUND

The exemplary embodiments described herein relates to optical analysis systems and methods for dry cements and, in particular, to systems and methods for analyzing the characteristics, including compositions, of a dry cement.

Set cement compositions are used in the oil and gas sector for many purposes including stabilizing wellbores and plugging wellbores. Set cements are produced from cement slurries that include water, dry cements, and optionally cement slurry additives. The operational parameters relating to the cement slurry and the characteristics of the resultant set cement are derived, at least in part, from the dry cement composition and the composition and concentration of the optional cement slurry additives.

Some types of dry cements (e.g., Portland cements) are classified and graded based on its composition. Dry cement classifications broadly characterize dry cements by the concentration of the major components (or analytes) in the dry cement. For example, the multitude of American Petroleum Institute ("API") classifications for Portland cements relate specifically to the relative concentration of four components $(CaO)_3.SiO_2$, $(CaO)_2.SiO_2$, $(CaO)_3.Al_2O_3$, and $(CaO)_3.Al_2O_3.Fe_2O_3$, whereas classifying Sorel cements may be based on the major components of $MgO$, $MgCl_2$, $ZnO$, $ZnCl_2$, and water.

Cement grades also relates to the composition of the dry cement, but to the minor components like metal compound concentration, sulfate concentration (e.g., sulfate salts), minor component oxide concentrations, and the like. The concentration of these minor components can affect the mechanical properties and setting chemistry of a set cement produced therefrom, which leads to variability within classifications of dry cements. For example, silicate minerals like $(CaO)_3.SiO_2$ may be used in grading a Sorel cement.

Classifying and grading a dry cement involves a complicated, multi-step process where harsh chemicals are mixed with the dry cement and then analyzed via expensive, time-consuming methods like x-ray diffraction and gravimetric analysis. Further, these classification and grading processes use equations and make assumptions that have been shown to introduce significant error into the analysis.

When the dry cement is incorrectly classified and graded, the incorrect composition and/or concentration of cement slurry additives may be used, resulting in an inefficient or ineffective cementing operation. In relation to downhole oil and gas operations, such cementing operations can increase both costs and the instances of remedial operations to repair the set cement.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
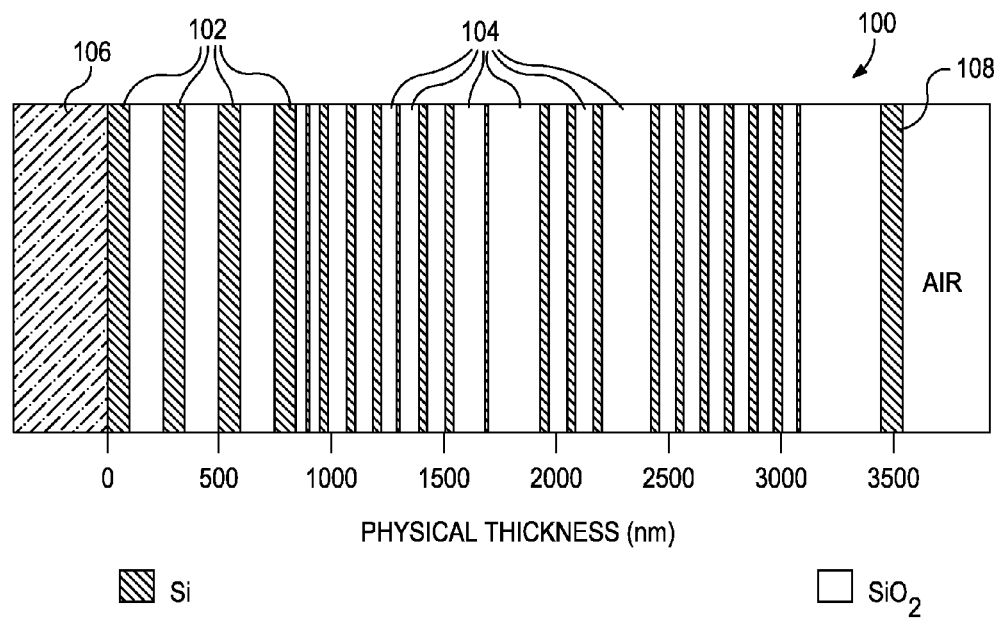
FIG. 1 illustrates an exemplary integrated computation element, according to one or more embodiments.

The exemplary embodiments described herein relates to optical analysis systems and methods for dry cements and, in particular, to systems and methods for analyzing the characteristics, including compositions, of a dry cement.

The exemplary systems and methods described herein employ various configurations of optical computing devices, also commonly referred to as "opticoanalytical devices," for the rapid analysis of dry cements. The disclosed systems and methods may be suitable for use in the oil and gas industry since the described optical computing devices provide a cost-effective, rugged, and accurate means for classifying and grading dry cements in order to facilitate the effective production of cement slurries and set cements in oil/gas applications. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a dry composition, especially to determine the quality of the dry composition.

The optical computing devices disclosed herein, which are described in more detail below, can advantageously provide rapid analysis of at least one characteristic of a dry cement (e.g., the composition of individual components in the dry cement or the particle size distribution in the dry cement). As described above, such a detailed analysis currently requires extensive time, high cost, and harsh chemicals and can give unreliable results. By contrast, the optical computing devices disclosed herein may provide rapid analysis of dry cements with minimal sample prep, if any. Additionally, because the analysis is rapid, multiple measurements may be taken to reduce error. Further, because of the small size and relatively low cost of the optical computing devices disclosed herein, the methods for analyzing dry cements presented herein may be suitable for not only laboratory use, but also, in-field analysis (e.g., at a manufacturing or mining site, at a distribution center, or at a well site).

A significant and distinct advantage of the optical computing devices disclosed herein is that they can be configured to specifically detect and/or measure a particular characteristic of interest of a dry cement, thereby allowing qualitative and/or quantitative analyses of the material of interest to occur without having to undertake a time-consuming sample processing procedure. With rapid analyses capabilities on hand, the exemplary systems and methods described herein may be able to classify and/or grade dry cements, determine the composition and/or concentration of cement slurry additives to enhance the implementation efficacy of the dry cement, provide some measure of proactive or responsive control over the quality of the dry cement, allow for the collection and archival of information relating to the dry cement in conjunction with operational information to optimize subsequent operations, and any combination thereof.

As used herein, the term "dry cement" refers to refers to a mixture of solid particles including at least some cement particles and is not hydrated beyond about ambient conditions (e.g., no additional water has been added). It should be noted that the term "dry cement" does not refer to set cements (e.g., that have been formed from a cement slurry).

Dry cements may comprise a single cement or comprise a blend of two or more cements. Examples of cements may include, but are not limited to, hydraulic cements, Portland cement, gypsum cements, pozzolan cements, calcium phosphate cements, high alumina content cements, silica cements, high alkalinity cements, shale cements, acid/base cements, magnesia cements (e.g., Sorel cements), zeolite cement systems, cement kiln dust cement systems, slag cements, micro-fine cements, bentonites, and the like, any derivative thereof, and any combination thereof. Examples of Portland cements may include, but are not limited to, Portland cements classified as Classes A, C, H, and G according to API and their equivalent, Ordinary Portland cements of Type I, I/II, III, and V according to ASTM, including combinations thereof. Examples of pozzolan cements may include, but are not limited to, fly ash, silica fume, granulated blast furnace slag, calcined shale, opaline shale, pumice, pumicite, diatomaceous earth, volcanic ash, tuft, cement kiln dust, and any combination thereof.

As used herein, the term "characteristic" refers to a chemical, mechanical, or physical property (quantitative or qualitative) of a material of interest (e.g., a dry cement or an analyte thereof). As used herein, the term "analyte" refers to a chemical component. The term analyte encompasses chemical components that are at least one of: present in the material of interest, may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical computing devices disclosed herein can include, for example, chemical composition (e.g., identity and concentration in total or of individual analytes), impurity content, pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of a material of interest.

Examples of analytes within a dry cement may include, but are not limited to, $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $SO_3$, $Ca(OH)_2$, $Al(OH)_4^-$, $H_4SiO_4$, free lime, inorganic salts (e.g., sodium, potassium, magnesium, and calcium salts of sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, water, and any combination thereof.

In some instances, the foregoing analytes may be used in classifying cements (i.e., as a major component) or as grading cements (i.e., as a minor components), which depends on the dry cement. As used herein, the "major component" of a dry cement refers to a component or analyte that identifies the type of dry cement (e.g., Portland cement versus Sorel cement or Type I Portland cement versus Type V Portland cement). As used herein, the "minor component" of a dry cement refers to a component or analyte that is not a major component. The terms "major component" and "minor component" do not necessarily relate to a concentration. For example, in Ordinary Grade, Class G Portland cement may have about 5% $CaO)_3.Al_2O_3$ as one of the major components and up to about 6% MgO as one of the minor components.

As used herein, the term "cement slurry additive" refers to an additive that can be included in a cement slurry with water and a dry cement. Cement slurry additives may be liquids or dry additives (e.g., powders). In some instances, the dry cement and at least one cement slurry additive (typically a dry additive) may be combined to form a mixture that can be used in preparing a cement slurry. The mixture may be prepared at a storage facility, manufacturing facility, laboratory, distribution center, at the well site, or in transit between any of these locations.

Examples of cement slurry additives may include, but are not limited to, set retarders, set accelerators, fillers (e.g., weighting agents, lightweight particles like glass beads, rubber particles, and the like), dispersants, gelling agents, and the like, and any combination thereof.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical computing device as well as other considerations known to those skilled in the art. In addition, emission and/or scattering by the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a dry cement.

The exemplary systems and methods described herein will include at least one optical computing device configured to measure at least one characteristics of a dry cement or analyte thereof. In some embodiments, the optical computing devices suitable for use in the exemplary embodiments described herein may be mobile or portable. In some embodiments, the optical computing devices suitable for use in the exemplary embodiments described herein may be a portion of tank, silo, vat, or the like that store, mix, or otherwise contain dry cement (e.g., in a wall).

An optical computing device may include an electromagnetic radiation source, at least one processing element (e.g., an integrated computational element), and at least one detector arranged to receive optically interacted light from the at least one processing element. However, in at least one embodiment, the electromagnetic radiation source may be omitted and instead the electromagnetic radiation may be derived from the material of interest itself. In some embodiments, the exemplary optical computing devices may be specifically configured for detecting, analyzing, and quantitatively measuring a particular characteristic of the material of interest. In other embodiments, the optical computing devices may be general purpose optical devices, with post-acquisition processing (e.g., through computer means) being used to specifically detect the characteristic of interest.

The presently described optical computing devices combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of interest. As a result, interfering signals are discriminated from those of interest by appropriate configuration of the optical computing devices, such that the optical computing devices provide a rapid response regarding the characteristic of interest as based on the detected output. In some embodiments, the detected output can be converted into a voltage that is distinctive of the magnitude of the characteristic of interest. The foregoing advantages and others make the optical computing devices particularly well suited for field use.

The optical computing devices can be configured to detect not only the composition and concentrations of an analyte in a material of interest, but they can also be configured to determine physical properties and other characteristics of the material of interest as well, based on their analysis of the electromagnetic radiation received from the substance. For example, the optical computing devices can be configured to determine the concentration of an analyte and correlate the determined concentration to a characteristic of the material of interest by using suitable processing means. As will be appreciated, the optical computing devices may be configured to detect as many characteristics as desired for a given material of interest. All that is required to accomplish the monitoring of multiple characteristics of interest is the incorporation of suitable processing and detection means within the optical computing device for each characteristic of interest (e.g., the concentration of an analyte, the particle size distribution, or the temperature). In some embodiments, the properties of the material of interest can be determined using a combination of characteristics of interest (e.g., a linear, non-linear, logarithmic, and/or exponential combination). Accordingly, the more characteristics that are detected and analyzed using the optical computing devices, the more accurately the properties of the material of interest will be determined. For example, properties of a dry cement that may be determined using optical computing devices described herein may include, but are not limited to, the absolute concentration of an analyte, the relative ratios of two or more analytes, the presence or absence of an analyte, and the like, and any combination thereof.

The optical computing devices described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is reflected from, transmitted through, or radiated from the material of interest. This information is often referred to as the spectral "fingerprint" of the material of interest. The optical computing devices described herein are capable of extracting the information of the spectral fingerprint of multiple characteristics of a material of interest (e.g., a dry cement blend or an analyte thereof), and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties (e.g., reactivity) of the monitored substance (e.g., a dry cement blend or an analyte thereof) in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a dry cement blend. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic of interest.

Figure 2:
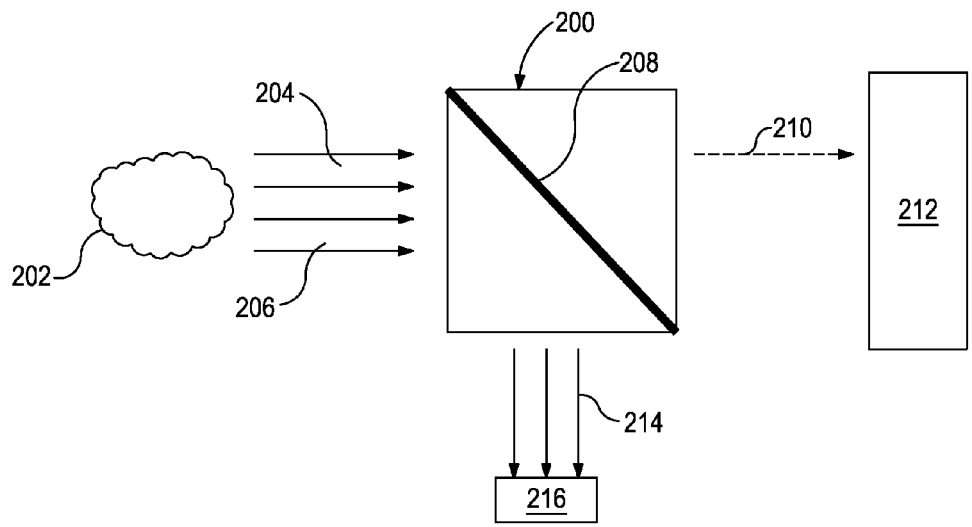
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a dry cement 202 produces an output of electromagnetic radiation (e.g., sample-interacted light), some of which is electromagnetic radiation 204 corresponding to the characteristic of interest and some of which is background electromagnetic radiation 206 corresponding to other characteristics of the dry cement 202. In some embodiments, the dry cement 202 may include one or more characteristics of interest that may correspond to the one or more analytes of the dry cement 202.

Although not specifically shown, one or more processing elements may be employed in the optical computing device 200 in order to restrict the optical wavelengths and/or bandwidths of the system and thereby eliminate unwanted electromagnetic radiation existing in wavelength regions that have no importance. Such processing elements can be located anywhere along the optical train, but are typically employed directly after a light source, which provides the initial electromagnetic radiation.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic of interest of the dry cement 202, may be conveyed to a detector 212 for analysis and quantification. In some embodiments, the detector 212 is configured to produce an output signal in the form of a voltage that corresponds to the particular characteristic of the dry cement 202. In at least one embodiment, the signal produced by the detector 212 and the characteristic of a dry cement 202 (e.g., concentration of an analyte) may be directly proportional. In other embodiments, the relationship may be a polynomial function, an exponential function, and/or a logarithmic function. The reflected optically interacted light 214, which may be related to other characteristics of the dry cement 202, can be directed away from detector 212. In alternative configurations, the ICE 208 may be configured such that the reflected optically interacted light 214 can be related to the characteristic of interest, and the transmitted optically interacted light 210 can be related to other characteristics in the dry cement 202.

In some embodiments, a second detector 216 can be present and arranged to detect the reflected optically interacted light 214. In other embodiments, the second detector 216 may be arranged to detect the electromagnetic radiation 204,206 derived from the dry cement 202 or electromagnetic radiation directed toward or before the dry cement 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204,206, and the transmitted or reflected electromagnetic radiation can then be directed to two or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of interest being analyzed using the optical computing device 200 can be further processed and/or analyzed computationally to provide additional characterization information about the dry cement 202 or an analyte thereof. In some embodiments, the identification and concentration of each analyte of interest in the dry cement 202 can be used to predict certain physical characteristics of the dry cement 202. For example, the bulk characteristics of the dry cement 202 (e.g., reactivity, set time, and the like) can be estimated by using a combination of the properties conferred to the dry cement 202 by each analyte. For example, the relative ratios of some of the analytes can indicate the concentration or range of concentration of cement slurry additives that should be used in preparing a cement slurry from the dry cement.

In some embodiments, the magnitude of the characteristic of interest determined using the optical computing device 200 can be fed into an algorithm operating under computer control. The algorithm may be configured to make predictions on how the characteristics of the dry cement 202 would change if the magnitude of the characteristic of interest are changed relative to one another. In some embodiments, the algorithm can produce an output that is readable by an operator who can manually take appropriate action, if needed, based upon the reported output. In other embodiments, however, the algorithm can take proactive process control. For example, in the production of some cements, the particles are heated in a kiln. Periodically monitoring the composition and concentration of analytes in the dry cement in the kiln may allow for changing the temperature of the kiln or length of time the dry cement is in the kiln to achieve a desired classification or grade of dry cement. In another example, in storage, the composition and concentration of analytes can be analyzed for a reduction in the quality of the dry cement. In some instances, the stored dry cement may be mixed with other dry cement to achieve a desired classification or grade of dry cement. By way of nonlimiting example, lime can degrade over time with exposure to carbon dioxide and, accordingly, may be an analyte of interest to analyze by such methods.

The algorithm can be part of an artificial neural network configured to use the concentration of each characteristic of interest in order to evaluate the overall characteristic(s) of the dry cement 202 and predict the composition and/or concentration of the cement slurry additives to be included to provide for desired properties in a resultant cement slurry. It is to be recognized that an artificial neural network can be trained using samples of predetermined characteristics of interest, and thereby generating a virtual library. As the virtual library available to the artificial neural network becomes larger, the neural network can become more capable of accurately predicting the characteristic of interest corresponding to a dry cement or analyte thereof. Furthermore, with sufficient training, the artificial neural network can more accurately predict the characteristics of the dry cement, even in the presence of unknown analytes.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
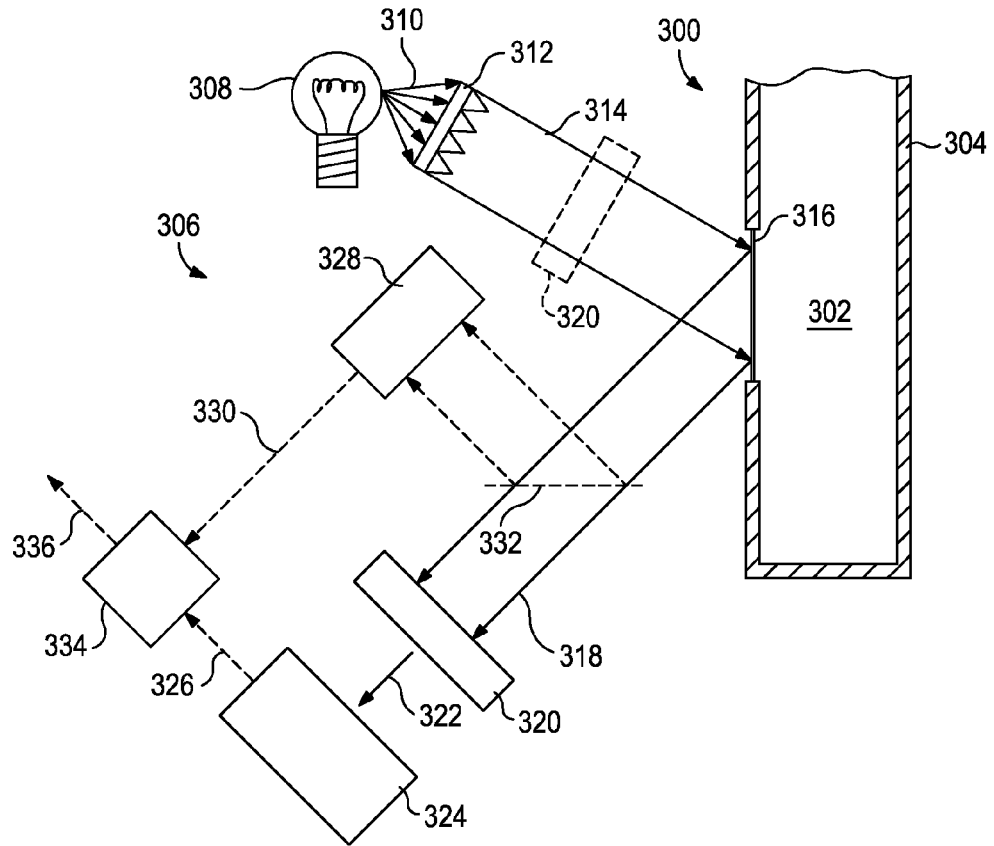
FIG. 3 illustrates an exemplary system for monitoring a dry cement present in a container, according to one or more embodiments.

Referring now to FIG. 3, illustrated is an exemplary system 300 for monitoring a dry cement 302, according to one or more embodiments. In the illustrated embodiment, the dry cement 302 may be contained within an exemplary container 304. In at least one embodiment, the container 304 may be a mixer and the dry cement 302 present therein may be actively mixing while measurements are being taken. In at least one embodiment, the container 304 may be a cup or the like of a mobile device. As will be appreciated, however, in other embodiments the container 304 may be any other type of container, as generally described or otherwise defined herein. For example, the container 304 may be a storage vessel or silo.

The system 300 may include at least one optical computing device 306, which may be similar in some respects to the optical computing device 200 of FIG. 2, and therefore may be best understood with reference thereto. While not shown, the device 306 may be housed within a casing or housing configured to substantially protect the internal components of the device 306 from damage or contamination from the external environment. The housing may operate to mechanically couple the device 306 to the container 304 with, for example, mechanical fasteners, brazing or welding techniques, adhesives, magnets, combinations thereof or the like.

As described in greater detail below, the optical computing device 306 may be useful in determining a particular characteristic of the dry cement 302 within the container 304, such as determining a concentration of an analyte present within the dry cement 302.

Knowing at least some of the characteristics of the dry cement 302 may help determine the overall composition of the dry cement 302. Knowing the composition of the dry cement 302 allows for a more accurate determination of the composition and/or concentration of cement slurry additives to use in a subsequent cement slurry. In turn, the cementing operation that utilized the cement slurry may be more effective as premature setting or delayed setting may be mitigated. Further, the resultant set cement may be of higher quality because the type of and concentration of additives was tailored to the original dry cement.

In some embodiments, the device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward the dry cement 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the dry cement 302 directly from the electromagnetic radiation source 308.

In one or more embodiments, the device 306 may also include a sampling window 316 arranged adjacent to or otherwise in contact with the dry cement 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like.

After passing through the sampling window 316, the electromagnetic radiation 310 impinges upon and optically interacts with the dry cement 302, including any analytes present within the dry cement 302. As a result, optically interacted radiation 318 is generated by and reflected from the dry cement 302. Those skilled in the art, however, will readily recognize that alternative variations of the device 306 may allow the optically interacted radiation 318 to be generated by being transmitted, scattered, diffracted, absorbed, emitted, or re-radiated by and/or from the dry cement 302, or one or more analytes present within the dry cement 302, without departing from the scope of the disclosure.

The optically interacted radiation 318 generated by the interaction with the dry cement 302 may be directed to or otherwise received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest of the dry cement 302. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to the dry cement 302. In other embodiments, the characteristic of interest corresponds to a particular analyte found in the dry cement 302.

It should be noted that, while FIG. 3 depicts the ICE 320 as receiving optically interacted radiation 318 from the dry cement 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE 320 components in the device 306 configured to cooperatively determine the characteristic of interest in the dry cement 302. For example, two or more ICE 320 may be arranged in series or parallel within the device 306 and configured to receive the optically interacted radiation 318 and thereby enhance sensitivities and detector limits of the device 306. In other embodiments, two or more ICE 320 may be arranged on a movable assembly, such as a rotating disc or an oscillating linear array, which moves such that the individual ICE 320 components are able to be exposed to or otherwise optically interact with electromagnetic radiation 310 for a distinct brief period of time. The two or more ICE 320 components in any of these embodiments may be configured to be either associated or disassociated with the characteristic of interest in the dry cement 302. In other embodiments, the two or more ICE 320 components may be configured to be positively or negatively correlated with the characteristic of interest.

In some embodiments, it may be desirable to monitor more than one characteristic of interest at a time using the device 306. In such embodiments, various configurations for multiple ICE 320 components can be used, where each ICE 320 component is configured to detect a particular and/or distinct characteristic of interest corresponding, for example, to the dry cement 302 or an analyte in the dry cement 302. In some embodiments, the characteristic of interest can be analyzed sequentially using multiple ICE 320 components that are provided a single beam of optically interacted radiation 318 being reflected from or transmitted through the dry cement 302. In some embodiments, as briefly mentioned above, multiple ICE 320 components can be arranged on a rotating disc, where the individual ICE 320 components are only exposed to the beam of optically interacted radiation 318 for a short time. Advantages of this approach can include the ability to analyze multiple characteristics of interest within the dry cement 302 using a single device 306 and the opportunity to assay additional characteristics simply by adding additional ICE 320 components to the rotating disc corresponding to those additional characteristics.

In other embodiments, multiple devices 306 can be placed at a single location along the container 304, where each device 306 contains a unique ICE 320 that is configured to detect a particular characteristic of interest. In such embodiments, a beam splitter can divert a portion of the optically interacted radiation 318 being reflected by, emitted from, or transmitted through the dry cement 302 and into each devices 306. Each devices 306, in turn, can be coupled to a corresponding detector (e.g., detector 320) or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two devices 306 may be arranged in series, such as being located on or within a movable housing configured to perform an analysis at a single location in the container 304. Likewise, multiple detection stations, each containing devices 306 in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the dry cement 302. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional.

In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beam splitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324, 328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326, 330 may entail computing a ratio of the two signals 326, 330. For example, the concentration or magnitude of each characteristic of interest determined using the optical computing device 306 can be fed into an algorithm run by the signal processor 334. The algorithm may be configured to make predictions on how the dry cement 302 in combination with cement slurry additives, optionally at varying concentrations, will behave in a cement slurry.

Systems similar to that illustrated in FIG. 3 may be useful in analyzing dry cements. For example, a system may include a probe that can be inserted into a dry cement for analysis of a characteristic thereof. As such, the dry cement may be contained within a container not having a device 306 connected thereto (e.g., a bag of dry cement as shipped from a distributor). Further, the dry cement may not be contained within a container, but rather may be a pile or mound of dry cement.

Figure 4:
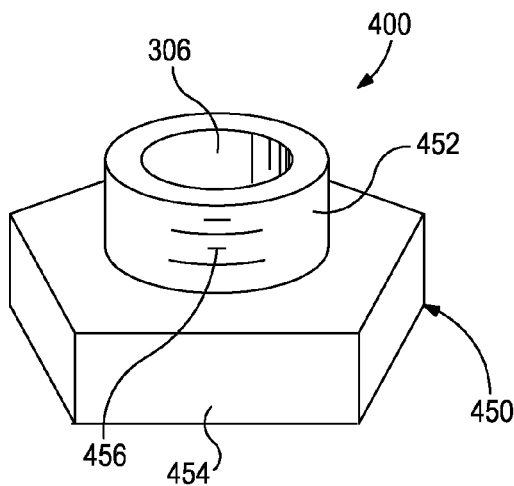
FIG. 4 illustrates an exemplary housing that may be used to house an optical computing device, according to one or more embodiments.

Referring now to FIG. 4, with continued reference to FIG. 3, illustrated is an exemplary housing 400 that may be used to house an optical computing device, according to one or more embodiments. In some embodiments, the housing 400 may be mechanically coupled to the container 304 using, for example, mechanical fasteners, brazing or welding techniques, adhesives, magnets, combinations thereof or the like. The housing 400 may be configured to substantially protect the internal components of the respective device 306 from damage or contamination from the external environment. Those skilled in the art, however, will readily recognize that several alternative designs and configurations of housings used to house the optical computing devices are suitable for the presently disclosed systems and methods. Indeed, the housing embodiments described and disclosed herein are by way of example only, and should not be considered limiting to the exemplary systems and methods disclosed herein.

As illustrated, the housing 400 may be in the general form of a bolt 450 which encloses the various components of an optical computing device, such as the device 306 of FIG. 3. In one embodiment, the components of the device 306 housed within the housing 400 may be generally housed within a stem 452 of the bolt 450, and the bolt 450 may have a hex head 454 for manual manipulation of the housing 400 using, for example, a wrench or other suitable torque-generating hand tool.

In at least one embodiment, the housing 400 defines external threads 456 that are threadable with corresponding mating pipe threads provided in, for example, an opening defined in the container 304 (FIG. 3) that is configured to receive the housing 400. The threads 456 may be sealed to the mating pipe threads with a thread sealant. The sampling window 316 is configured to be in optical communication with the dry cement 302 (FIG. 3) and allows optical interaction between the dry cement 302 and the other internal components of the internally-housed device 306.

Referring again to FIG. 3, those skilled in the art will readily recognize that, in one or more embodiments, electromagnetic radiation may be derived from the dry cement 302 itself, and otherwise derived independent of the electromagnetic radiation source 308. For example, various substances naturally radiate electromagnetic radiation that is able to optically interact with the ICE 320. In some embodiments, for example, the dry cement 302 or the substance within the dry cement 302 may be a blackbody radiating substance configured to radiate heat that may optically interact with the ICE 320. In other embodiments, the dry cement 302 or the substance within the dry cement 302 may be radioactive or chemo-luminescent and, therefore, radiate electromagnetic radiation that is able to optically interact with the ICE 320. In yet other embodiments, the electromagnetic radiation may be induced from the dry cement 302 or the substance within the dry cement 302 by being acted upon mechanically, magnetically, electrically, combinations thereof, or the like. For instance, in at least one embodiment, a voltage may be placed across the dry cement 302 or the substance within the dry cement 302 in order to induce the electromagnetic radiation. As a result, embodiments are contemplated herein where the electromagnetic radiation source 308 is omitted from the particular optical computing device.

Some embodiments may involve optically interacting a dry cement with one or more integrated computational elements, wherein each integrated computational element is configured to detect a characteristic of the dry cement; generating a plurality of output signals corresponding to each of the characteristics of the dry cement detected by the one or more integrated computational elements; receiving and processing each of the plurality of output signals with at least one signal processor to yield a value for each of the characteristics of the dry cement; and classifying (or grading or both) the dry cement based on the values of each of the characteristics of the dry cement.

For example, in some instances for classifying Portland cements, gypsum cements, and some hydraulic cements, the characteristic of the dry cement may be at least one selected from the group of a concentration of $(CaO)_3.SiO_2$, a concentration of $(CaO)_2.SiO_2$, a concentration of $(CaO)_3.Al_2O_3$, a concentration of $(CaO)_3.Al_2O_3.Fe_2O_3$, and any combination thereof. In another example, in some instances for classifying, the characteristic of the dry cement may be a relative concentration ratio of at least two selected from the group of $(CaO)_3.SiO_2$, $(CaO)_2.SiO_2$, $(CaO)_3.Al_2O_3$, and $(CaO)_3.Al_2O_3.Fe_2O_3$.

In yet another example, in some instances for classifying Sorel cements, the characteristic of the dry cement may be at least one selected from the group of a concentration of MgO, a concentration of $MgCl_2$, a concentration of ZnO, a concentration of $ZnCl_2$, a concentration of water, and any combination thereof. In another example, in some instances for classifying Sorel cements, the characteristic of the dry cement may be a relative concentration ratio of at least two selected from the group of MgO, $MgCl_2$, ZnO, $ZnCl_2$, and water.

In yet another example, in some instances for classifying calcium phosphate cements, the characteristic of the dry cement may be at least one selected from the group of a concentration of CaO, a concentration of phosphate, a concentration of hydroxide, a concentration of water, and any combination thereof. In another example, in some instances for classifying calcium phosphate cements, the characteristic of the dry cement may be a relative concentration ratio of CaO to phosphate. Further, in some instances for classifying, the characteristic of the dry cement may be a relative concentration ratio of water to hydroxide.

One of ordinary skill in the art will recognize the major components that should be analyzed for the various examples of dry cements.

In yet another example, in some instances for grading, the characteristic of the dry cement may be a concentration of at least one selected from the group of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $SO_3$, $Ca(OH)_2$, $Al(OH)_4^-$, $H_4SiO_4$, free lime, inorganic salts (e.g., sodium, potassium, magnesium, and calcium salts of sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, water, and any combination thereof.

In some instances, reporting the classification and grade of the dry cement may be according to API or ASTM classifications/grades. In some instances, reporting the classification and grade of the dry cement may be a listing of at least some of the analytes in the dry cement and their respective concentration and/or relative ratios.

Some embodiments may involve classifying (and optionally grading) the dry cement based on the values of each of the characteristics of the dry cement as described herein; and determining a concentration and/or a composition of a cement slurry additive to be used in conjunction with the dry cement based on the characteristic of interest. Some embodiments may involve optically interacting a dry cement with two or more integrated computational elements, wherein each integrated computational element is configured to detect a characteristic of the dry cement; generating a plurality of output signals corresponding to each of the characteristics of the dry cement detected by the two or more integrated computational elements; receiving and processing each of the plurality of output signals with at least one signal processor to yield a value for each of the characteristics of the dry cement; and determining a concentration and/or a composition of a cement slurry additive to be used in conjunction with the dry cement based on the characteristic of interest (e.g., a concentration of at least one analyte, a relative ratio of two or more analytes, the presence or absences of an analyte, or particle size distribution of the particles in the dry cement). In some instances, it may not be necessary to explicitly classify or grade the dry cement to determine a concentration and/or a composition of a cement slurry additive to be used in conjunction with the dry cement, described further herein.

In some instances, determining the concentration and/or the composition of the cement slurry additive may use computers and optionally artificial neural networks.

One skilled in the art would understand the appropriate concentration and/or composition of a cement slurry additive based on the composition of analytes and their relative ratios present in the dry cement. For example, dry cements that comprise more free lime may benefit from a higher concentration of set retarder additives. In another example, dry cements that comprise higher concentrations of copper and/or zinc may benefit from additives to enhance the compressive strength of the resultant set cement. In yet another example, the level of sulfate (e.g., sulfate salts) or another suitable additive may be adjusted in response to the concentration of $(CaO)_3.Al_2O_3$ in to enhance fluidity. In another example, the concentration of $K_2O$ and $Na_2O$ in the dry cement effect the reactivity of $(CaO)_3.Al_2O_3$. Specifically, $K_2O$ increases the activity of $(CaO)_3.Al_2O_3$ while $Na_2O$ decreases the activity. Sulfate (e.g., sulfate salts) and other additives may be added in appropriate concentration to counteract both oxides. In yet another example, high levels of free CaO and MgO can result in too much expansion in the set cement, which can be an avenue to failure of the set cement. Addition of sodium chloride, magnesium chloride, calcium chloride, calcium fluoride, and other additives may be added to the dry cement (during or after manufacturing of the dry cement) to address this issue. In another example, particle size may be useful in determining a composition or concentration of cement slurry additive to be used. For example, larger particle sizes that can lead to a reduced strength set cement may benefit from a strengthening cement slurry additive (e.g., fibers or other resilient particles). In another example, small particle sizes may benefit from more water to completely hydrate because of the increased surface area.

Some embodiments may involve determining a concentration and/or a composition of a cement slurry additive as described herein; and preparing a mixture that comprises the dry cement and the cement slurry additive based on the determined concentration and be determined composition. Some embodiments may further involve implementing the mixture in a wellbore operation (e.g., a primary cementing operation, a secondary cementing operation, or a remedial cementing operation).

Some embodiments may involve determining a concentration and/or a composition of a cement slurry additive as described herein; and preparing a kit comprise the dry cement and an additive compositions and concentration guide (e.g., in the form of a table) based on the determined concentration and be determined composition. A kit may be in any suitable form (e.g., a bag of the mixture with a guide/table on the bag).

Some embodiments may involve optically interacting a dry cement with one or more integrated computational elements, wherein each integrated computational element is configured to detect a characteristic of the dry cement; generating a plurality of output signals corresponding to each of the characteristics of the dry cement detected by the one or more integrated computational elements; receiving and processing each of the plurality of output signals with at least one signal processor to yield a value for each of the characteristics of the dry cement; and modifying the dry cement based on the values of each of the characteristics of the dry cement. In some instances, modifying may involve blending the dry cement with a second dry cement (e.g., to alter the relative concentration of major components in the dry cement). In some instances, modifying may involve changing the particle size distribution of the dry cement. In some instances, modifying (e.g., during manufacturing) may involve changing the kiln temperature. One of ordinary skill in the art would recognize other suitable modifications that can be made to the dry cement based on the characteristic of interest to achieve a desired dry cement.

In some instances, hybrids of the foregoing methods may be suitable. For example, some embodiments may involve both modifying the dry cement blend and determining a concentration/composition of a cement slurry to add to the dry cement blend after modification. In another example, some embodiments may involve both modifying the dry cement blend and classifying, grading, or both a cement slurry after modification. In yet another example, some embodiments may involve classifying, grading, or both a cement slurry to add to the dry cement blend; modifying the dry cement blend; and re-classifying, re-grading, or both a cement slurry after modification. In some embodiments, each of the foregoing may involve producing a mixture (e.g., a cement slurry) and implementing the mixture in a primary cementing operation, a secondary cementing operation, or a remedial cementing operation in a wellbore.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

Embodiments disclosed herein include:

A. a method that includes optically interacting a dry cement with an ICE configured to detect a characteristic of the dry cement; generating a plurality of output signals corresponding to the characteristic of the dry cement detected by the ICE; receiving and processing the plurality of output signals with a signal processor to yield a value for the characteristic of the dry cement; and determining at least one of a composition and a concentration of a cement slurry additive for use in combination with the dry cement based on the value of the characteristic of the dry cement;

B. a method that includes optically interacting a dry cement with a first ICE configured to detect a concentration of $(CaO)_3.SiO_2$, wherein the dry cement is a Portland cement, a hydraulic cement, or a gypsum cement; optically interacting the dry cement with a second ICE configured to detect a concentration of $(CaO)_2.SiO_2$; optically interacting a dry cement with a third ICE configured to detect a concentration of $(CaO)_3.Al_2O_3$; optically interacting a dry cement with a fourth ICE configured to detect a concentration of $(CaO)_3.Al_2O_3.Fe_2O_3$; generating a plurality of output signals corresponding to each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; receiving and processing each of the plurality of output signals with at least one signal processor to yield a value for each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; and classifying the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$.

C. a method that includes optically interacting a dry cement with an ICE configured to detect a characteristic of the dry cement, wherein the dry cement comprises a minor component selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-H_4SiO_4$, a sulfate salt, a phosphate salt, a carbonate salt, a sodium salt, a potassium salt, free lime, a metal containing compound, hydroxide, water, and any combination thereof; and wherein the characteristic of the dry cement is a concentration of the minor component; generating a plurality of output signals corresponding to the characteristic of the dry cement detected by the ICE; receiving and processing the plurality of output signals with a signal processor to yield a value for the characteristic of the dry cement; and grading the dry cement based on the value of the for the characteristic of the dry cement Embodiment A may have one or more of the following additional elements in any combination: Element 1: wherein the characteristic of the dry cement is a concentration of one selected from the group consisting $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-H_4SiO_4$, a sulfate salt, a phosphate salt, a carbonate salt, a sodium salt, a potassium salt, free lime, a metal containing compound, hydroxide, and water; Element 2: wherein the characteristic of the dry cement is particle size distribution; Element 3: wherein the dry cement is a Portland cement, a hydraulic cement, or a gypsum cement; and wherein the characteristic of the dry cement is a concentration of one selected from the group consisting of $(CaO)_3.SiO_2$, $(CaO)_2.SiO_2$, $(CaO)_3.Al_2O_3$, and $(CaO)_3.Al_2O_3.Fe_2O_3$; Element 4: wherein the dry cement is a Portland cement, a hydraulic cement, or a gypsum cement; and wherein the characteristic of the dry cement is a concentration of one selected from the group consisting of a cadmium compound, a zinc compound, a nickel compound, a copper compound, a lead compound, a sulfate salt, a phosphate salt, a carbonate salt, a sodium salt, and a potassium salt; Element 5: wherein the dry cement is a Sorel cement; and wherein the characteristic of the dry cement is a concentration of one selected from the group consisting of MgO, $MgCl_2$, ZnO, $ZnCl_2$, and water; Element 6: wherein the dry cement is a calcium phosphate cement; and wherein the characteristic of the dry cement is a concentration of one selected from the group consisting of CaO, phosphate, water, and hydroxide; Element 7: wherein the characteristic of the dry cement is a first characteristic of the dry cement; optically interacting the dry cement with a second ICE configured to detect a second characteristic of the dry cement that is different than the first characteristic of the dry cement; generating a plurality of second output signals corresponding to the second characteristic of the dry cement detected by the second ICE; receiving and processing the plurality of second output signals with the signal processor to yield a value for the second characteristic of the dry cement; and wherein determining the at least one of a composition and a concentration of the cement slurry additive for use in combination with the dry cement is based on the values for the first and second characteristics of the dry cement; Element 8: Element 7 wherein the second characteristic of the dry cement is a concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-H_4SiO_4$, a sulfate salt, a phosphate salt, a carbonate salt, a sodium salt, a potassium salt, free lime, a metal containing compound, hydroxide, and water; Element 9: Element 8 where the method further includes grading the dry cement based on the concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-H_4SiO_4$, the sulfate salt, the phosphate salt, the carbonate salt, the sodium salt, the potassium salt, free lime, the metal containing compound, hydroxide, and water; Element 10: the method further including preparing a mixture comprising the dry cement and the cement slurry additive; Element 11: Element 10 wherein the method further includes implementing the mixture in a primary cementing operation, a secondary cementing operation, or a remedial cementing operation in a wellbore; and Element 12: modifying the dry cement based on based on the value of the characteristic of the dry cement. Exemplary combinations of these optional elements include, but are not limited to, one of Elements 1-6 in combination with Element 7 and optionally Element 8 and optionally Element 9; any of the foregoing in combination with Element 10 and optionally Element 11; one of Elements 1-6 in combination with Element 10 and optionally Element 11; Element 7 and optionally Element 8 (and optionally Element 9) in combination with Element 10 and optionally Element 11; one of Elements 1-6 in combination with Element 10 and optionally Element 11; and Element 12 in combination with any of the foregoing; and one of Elements 1-6 in combination with Element 12.

Embodiment B may have one or more of the following additional elements in any combination: Element 13: wherein a fifth ICE is configured to detect a concentration of one selected from the group consisting of a cadmium compound, a zinc compound, a nickel compound, a copper compound, a lead compound, a sulfate salt, a phosphate salt, a carbonate salt, a sodium salt, and a potassium salt; Element 14: Element 13 where the method further includes determining at least one of a composition and a concentration of a cement slurry additive for use in combination with the dry cement based on the concentration of one selected from the group consisting of the cadmium compound, the zinc compound, the nickel compound, the copper compound, the lead compound, the sulfate salt, the phosphate salt, the carbonate salt, the sodium salt, and the potassium salt; Element 15: Element 13 where the method further includes modifying the dry cement based on based on the concentration of one selected from the group consisting of the cadmium compound, the zinc compound, the nickel compound, the copper compound, the lead compound, the sulfate salt, the phosphate salt, the carbonate salt, the sodium salt, and the potassium salt; Element 16: the method further including determining at least one of a composition and a concentration of a cement slurry additive for use in combination with the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; Element 17: Element 14 or Element 16 wherein the method further includes preparing a mixture comprising the dry cement and the cement slurry additive; and Element 18: Element 17 wherein the method further includes implementing the mixture in a primary cementing operation, a secondary cementing operation, or a remedial cementing operation in a wellbore; and Element 19: modifying the dry cement based on based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$. Exemplary combinations of these optional elements include, but are not limited to, Elements 13, 14, and 16 in combination wherein the cement slurry additive is determined based on one characteristic of Element 13 and one characteristic of Element 16; Element 17 in combination with the foregoing; Element 18 in combination with the foregoing; and Element 13 and 15 in combination with Element 19.

Embodiment C may have one or more of the following additional elements in any combination: Element 20: the method further including determining at least one of a composition and a concentration of a cement slurry additive for use in combination with the dry cement based on the value of the for the characteristic of the dry cement; Element 21: Element 20 where the method further includes preparing a mixture comprising the dry cement and the cement slurry additive; and Element 22: the method further including modifying the dry cement based on the value of the for the characteristic of the dry cement. Exemplary combinations of these optional elements include, but are not limited to, Elements 20-22 in combination and Elements 20 and 22 in combination.

Therefore, the exemplary embodiments described herein is well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method comprising:
   optically interacting a dry cement with an integrated computational element ("ICE") configured to detect a characteristic of the dry cement;
   generating a plurality of output signals corresponding to the characteristic of the dry cement detected by the ICE;
   receiving and processing the plurality of output signals with a signal processor to yield a value for the characteristic of the dry cement; and
   determining at least one of a composition and a concentration of a cement slurry additive for use in combination with the dry cement based on the value of the characteristic of the dry cement.

2. The method of claim 1, wherein the characteristic of the dry cement is a concentration of one selected from the group consisting $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4{}^-H_4SiO_4$, a sulfate salt, a phosphate salt, a carbonate salt, a sodium salt, a potassium salt, free lime, a metal containing compound, hydroxide, and water.

3. The method of claim 1, wherein the characteristic of the dry cement is particle size distribution.

4. The method of claim 1, wherein the dry cement is a Portland cement, a hydraulic cement, or a gypsum cement, and wherein the characteristic of the dry cement is a concentration of one selected from the group consisting of $(CaO)_3.SiO_2$, $(CaO)_2.SiO_2$, $(CaO)_3.Al_2O_3$, and $(CaO)_3.Al_2O_3.Fe_2O_3$.

5. The method of claim 1, wherein the dry cement is a Portland cement, a hydraulic cement, or a gypsum cement, and wherein the characteristic of the dry cement is a concentration of one selected from the group consisting of a cadmium compound, a zinc compound, a nickel compound, a copper compound, a lead compound, a sulfate salt, a phosphate salt, a carbonate salt, a sodium salt, and a potassium salt.

6. The method of claim 1, wherein the dry cement is a Sorel cement, and wherein the characteristic of the dry cement is a concentration of one selected from the group consisting of MgO, $MgCl_2$, ZnO, $ZnCl_2$, and water.

7. The method of claim 1, wherein the dry cement is a calcium phosphate cement, and wherein the characteristic of the dry cement is a concentration of one selected from the group consisting of CaO, phosphate, water, and hydroxide.

8. The method of claim 1, wherein the characteristic of the dry cement is a first characteristic of the dry cement, the method further comprising:
   optically interacting the dry cement with a second ICE configured to detect a second characteristic of the dry cement that is different than the first characteristic of the dry cement;

generating a plurality of second output signals corresponding to the second characteristic of the dry cement detected by the second ICE; and receiving and processing the plurality of second output signals with the signal processor to yield a value for the second characteristic of the dry cement, wherein determining the at least one of a composition and a concentration of the cement slurry additive for use in combination with the dry cement is based on the values for the first and second characteristics of the dry cement.

9. The method of claim 8, wherein the second characteristic of the dry cement is a concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4{}^-H_4SiO_4$, a sulfate salt, a phosphate salt, a carbonate salt, a sodium salt, a potassium salt, free lime, a metal containing compound, hydroxide, and water.

10. The method of claim 1, further comprising:
preparing a mixture comprising the dry cement and the cement slurry additive.

11. The method of claim 10, further comprising:
implementing the mixture in a primary cementing operation, a secondary cementing operation, or a remedial cementing operation in a wellbore.

12. A method comprising:
optically interacting a dry cement with a first integrated computational element ("ICE") configured to detect a concentration of $(CaO)_3.SiO_2$, wherein the dry cement is a Portland cement, a hydraulic cement, or a gypsum cement;
optically interacting the dry cement with a second ICE configured to detect a concentration of $(CaO)_2.SiO_2$;
optically interacting the dry cement with a third ICE configured to detect a concentration of $(CaO)_3.Al_2O_3$;
optically interacting the dry cement with a fourth ICE configured to detect a concentration of $(CaO)_3.Al_2O_3.Fe_2O_3$;
generating a plurality of output signals corresponding to each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$;
receiving and processing each of the plurality of output signals with at least one signal processor to yield a value for each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; and
classifying the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$.

13. The method of claim 12 further comprising:
optically interacting the dry cement with a fifth ICE is configured to detect a concentration of one selected from the group consisting of a cadmium compound, a zinc compound, a nickel compound, a copper compound, a lead compound, a sulfate salt, a phosphate salt, a carbonate salt, a sodium salt, and a potassium salt;
generating a plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt;

receiving and processing the plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt with the at least one signal processor to yield a value for the concentration of one selected from the group consisting of the cadmium compound, the zinc compound, the nickel compound, the copper compound, the lead compound, the sulfate salt, the phosphate salt, the carbonate salt, the sodium salt, and the potassium salt; and grading classifying the dry cement based on the value for the concentration of one selected from the group consisting of the cadmium compound, the zinc compound, the nickel compound, the copper compound, the lead compound, the sulfate salt, the phosphate salt, the carbonate salt, the sodium salt, and the potassium salt.

14. The method of claim 12 further comprising:
determining at least one of a composition and a concentration of a cement slurry additive for use in combination with the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$.

15. The method of claim 14 further comprising:
preparing a mixture comprising the dry cement and the cement slurry additive.

16. The method of claim 12 further comprising:
modifying the dry cement based on based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$.

17. A method comprising:
optically interacting a dry cement with an integrated computational element ("ICE") configured to detect a characteristic of the dry cement, wherein the dry cement comprises a minor component selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4{}^-H_4SiO_4$, a sulfate salt, a phosphate salt, a carbonate salt, a sodium salt, a potassium salt, free lime, a metal containing compound, hydroxide, water, and any combination thereof; and wherein the characteristic of the dry cement is a concentration of the minor component;
generating a plurality of output signals corresponding to the characteristic of the dry cement detected by the ICE;
receiving and processing the plurality of output signals with a signal processor to yield a value for the characteristic of the dry cement; and
grading the dry cement based on the value of the characteristic of the dry cement.

18. The method of claim 17 further comprising:
determining at least one of a composition and a concentration of a cement slurry additive for use in combination with the dry cement based on the value of the characteristic of the dry cement.

19. The method of claim 18 further comprising:
preparing a mixture comprising the dry cement and the cement slurry additive.

20. The method of claim 17 further comprising:
modifying the dry cement based on the value of the characteristic of the dry cement.

* * * * *